United States Patent
Bolea (10) Patent No.: US 9,809,836 B2
(45) Date of Patent: Nov. 7, 2017

(54) METHOD OF DIFFERENTIATING MICROBIAL COLONIES IN AN IMAGE

(71) Applicant: 3M INNOVATIVE PROPERTIES COMPANY, Saint Paul, MN (US)

(72) Inventor: Phillip A. Bolea, Grant, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 15/590,193

(22) Filed: May 9, 2017

(65) Prior Publication Data
US 2017/0240947 A1 Aug. 24, 2017

Related U.S. Application Data

(63) Continuation of application No. 14/652,366, filed as application No. PCT/US2013/074882 on Dec. 13, 2013, now Pat. No. 9,677,108.

(60) Provisional application No. 61/739,786, filed on Dec. 20, 2012.

(51) Int. Cl.
 *G06K 9/00* (2006.01)
 *C12Q 1/04* (2006.01)
 *G01N 33/569* (2006.01)

(52) U.S. Cl.
 CPC .......... *C12Q 1/04* (2013.01); *G01N 33/569* (2013.01); *G06K 9/00134* (2013.01); *G06K 9/00147* (2013.01)

(58) Field of Classification Search
 None
 See application file for complete search history.

(56) References Cited

U.S. PATENT DOCUMENTS

| 4,565,783 | A | 1/1986 | Hansen et al. |
| 5,089,413 | A | 2/1992 | Nelson et al. |
| 5,364,766 | A | 11/1994 | Mach et al. |
| 5,510,246 | A | 4/1996 | Morgan ............ C12Q 1/04 377/10 |
| 5,601,998 | A | 2/1997 | Mach et al. |
| 5,681,712 | A | 10/1997 | Nelson |

(Continued)

FOREIGN PATENT DOCUMENTS

| EP | 2 520 923 | 11/2012 |
| FR | 2 926 820 | 7/2009 |

(Continued)

OTHER PUBLICATIONS

US 4,476,226, 10/1984, Hansen et al. (withdrawn)

(Continued)

*Primary Examiner* — Shervin Nakhjavan (57) ABSTRACT

A method of identifying microbial colonies in a culture device is provided. The method comprises using an imaging device to produce a first image of a thin film culture device while providing illumination to a front side of the device and to produce a second image of the thin film culture device while providing illumination to a back side of the device. The method further comprises analyzing the first and second images to identify microorganism colonies in each image, analyzing the first and second images values of a size parameter for a colony at a particular location in the culture device, and comparing the values. The method can be used to differentiate and count at least two colony types.

13 Claims, 6 Drawing Sheets

(56) References Cited

U.S. PATENT DOCUMENTS

| | | | |
|---|---|---|---|
| 6,058,209 | A | 5/2000 | Vaidyanathan et al. |
| 6,243,486 | B1 | 6/2001 | Weiss |
| 6,251,624 | B1 | 6/2001 | Matsumura ............... C12Q 1/04 435/29 |
| 7,298,885 | B2 * | 11/2007 | Green ................. G06K 9/00127 382/133 |
| 7,496,225 | B2 | 2/2009 | Graessle et al. |
| 7,947,575 | B2 | 5/2011 | Dunne et al. |
| 8,094,916 | B2 | 1/2012 | Graessle ............ G01N 15/1475 382/133 |
| 2004/0092001 | A1 | 5/2004 | Bedingham ............ C12M 33/04 435/286.2 |
| 2004/0253660 | A1 | 12/2004 | Gibbs .................... C12Q 1/045 435/34 |
| 2005/0053265 | A1 | 3/2005 | Graessle et al. |
| 2005/0053266 | A1 | 3/2005 | Plumb ................ G06K 9/00127 382/128 |
| 2005/0208539 | A1 | 9/2005 | Vann ................. B01L 3/502707 435/6.11 |
| 2009/0197298 | A1 | 8/2009 | Rambach |
| 2011/0102582 | A1 | 5/2011 | Graessle ............ G01N 15/1475 348/135 |
| 2011/0151501 | A1 * | 6/2011 | Bolea ..................... C12M 23/44 435/34 |
| 2012/0028251 | A1 * | 2/2012 | Mach ....................... C12Q 1/04 435/6.1 |
| 2013/0242083 | A1 | 9/2013 | Potts .................. G01N 21/8806 348/125 |
| 2013/0258092 | A1 | 10/2013 | Hallset ................. B08B 9/0321 348/81 |
| 2014/0161330 | A1 * | 6/2014 | Allano ................. G01N 21/255 382/128 |

FOREIGN PATENT DOCUMENTS

| | | |
|---|---|---|
| WO | WO 96/18167 | 6/1996 |
| WO | WO 96/18720 | 6/1996 |
| WO | WO 98/59314 | 12/1998 |
| WO | WO 2005/062744 | 7/2005 |

OTHER PUBLICATIONS

Bae, E. et al.; "Portable bacterial identification system based on elastic light scatter patterns"; Journal of Biological Engineering; vol. 6, No. 12; 2012; 12 pgs.

Corkidi, G et al.; "Covasiam: an Image Analysis Method That Allows Detection of Confluent Microbial Colonies and Colonies of Various Sizes for Automated Counting"; Applied and Environmental Microbiology; vol. 64; No. 4; 1998; pp. 1400-1404 (XP003001000).

Marotz, J. et al.; "Effective object recognition for automated counting of colonies in Petri dishes (automated colony counting)[1] "; Computer Methods and Programs in Biomedicine; vol. 66; 2001; pp. 183-198 (XP009160165).

Wang, W.; "Colony image acquisition system and segmentation algorithms"; Optical Engineering; vol. 50, No. 12; 2011; pp. 123001-1-123001-9.

Brochure entitled "Interpretation Guide—3M™ Petrifilm™ *E. coli* and Coliform Count Plates"; 2008; retrieved from the internet URL:http://jornades.uab.cat/workshopmrama/sites/jornades.uab.cat.workshopmrame/files/Petriflim_guides.pdf; retrieved Feb. 14, 2014; see p. 23 (XP055102418).

\* cited by examiner

METHOD OF DIFFERENTIATING MICROBIAL COLONIES IN AN IMAGE

CROSS REFERENCE TO RELATED APPLICATIONS

This application is a continuation of U.S. patent application Ser. No. 14/652,366, filed Jun. 15, 2015, which is a national stage filing under 35 U.S.C. 371 of International Patent Application No. PCT/US2013/074882, filed Dec. 13, 2013, which claims priority to U.S. Provisional Patent Application No. 61/739,786, filed Dec. 20, 2012, the disclosures of which are incorporated by reference in their entirety herein.

BACKGROUND

Biological safety is a paramount concern in modern society. Testing for biological contamination in foods or other materials has become an important and often mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

A wide variety of culture devices have been developed. As one example, culture devices have been developed by 3M Company (hereafter "3M") of St. Paul, Minn. In particular, culture devices are sold by 3M under the trade name PETRIFILM plates. Culture devices can be utilized to facilitate the rapid growth and detection of microorganisms commonly associated with food contamination, including, for example, aerobic bacteria, *E. coli*, coliform, enterobacteria, yeast, mold, *Staphylococcus aureus*, *Listeria*, *Campylobacter*, and the like. The use of PETRIFILM plates, or other growth media, can simplify bacterial testing of food samples.

Culture devices can be used to enumerate or identify the presence of bacteria so that corrective measures can be performed (in the case of food testing) or proper diagnosis can be made (in the case of medical use). In other applications, culture devices may be used to rapidly grow microorganisms in laboratory samples, e.g., for experimental purposes.

Biological scanning units refer to devices used to scan and/or count microbial colonies. For example, a food sample or laboratory sample can be placed on a culture device, and then the plate can be inserted into an incubation chamber. After incubation, the culture device can be placed into the biological scanning unit for automated detection and enumeration of bacterial growth. In this manner, biological scanning units automate the detection and enumeration of microbial colonies in a culture device, and thereby improve the biological testing process by reducing human error.

SUMMARY

In general, the present disclosure is directed to a technique for distinguishing objects in a scanned image. In particular, the technique is used to differentiate two microorganism colony types that are present in a culture medium that includes two indicator compounds with which each type of microorganism may react. In addition, the technique further may be used to count the number of colonies of each microorganism type in the scanned image of the culture device. To count the colonies, a culture device containing the culture medium is inserted into a scanning unit. Upon insertion of the culture device, the scanning unit generates an image of the culture device. Then, the number of microorganism colonies can be counted or otherwise determined using image processing and analysis routines performed either within the scanning unit or by an external computing device, such as a desktop computer, workstation or the like. In accordance with the invention, a method of distinguishing colony types is described. The method can be used to improve the accuracy over existing methods of automated counts of microorganism colonies in a scanned image.

In one aspect, the present disclosure provides a method. The method can comprise using an imaging device to produce a first image of a thin film culture device, the culture device having a front side having a transparent film cover sheet and a back side having a translucent substrate; using the imaging device to produce a second image of the thin film culture device, wherein the second image is produced while providing illumination to the back side of the device; analyzing the first and second images to identify microorganism colonies in each image; analyzing the first image to calculate a first value of a size parameter for a colony at a particular location in the culture device; analyzing the second image to calculate a second value of the size parameter at the particular location in the culture device; and comparing the first value to the second value. The first image is produced while providing illumination to the front side of the device. The culture device comprises first and second indicator compounds, wherein the first indicator compound is converted by a microorganism to a first product having a first color, wherein the second indicator compound is converted by a microorganism to a water-diffusible second product that forms a second color.

In any of the above embodiments, the first image can be produced while illuminating the device with a first ratio of front-side illumination to back-side illumination and the second image can be produced while illuminating the device with a second ratio of front-side illumination to back-side illumination that is lower than the first ratio. In some embodiments, the first ratio can be greater than 1:1. In some embodiments, the first ratio can be about 100%:0%. In some embodiments, the second ratio can be about 0%:100%.

In any of the above embodiments, the method further can comprise using the first or second image to count a number of microorganism colonies in the culture device. In any of the above embodiments, the method further can comprise using the first and second image to count a number of first type colonies and count a number of second type colonies in the culture device. In some embodiments, the first type colonies can convert the first indicator to the first product. In some embodiments, the second type colonies convert the second indicator to the second product.

In any of the above embodiments, the first indicator compound can comprise a tetrazolium dye. In any of the above embodiments, the second indicator compound can comprise a chromogenic enzyme substrate that includes an indolyl group. In any of the above embodiments, the size parameter can be an observed colony diameter. In some embodiments, the colony diameter can be a colony minimum diameter.

In another aspect, the present disclosure provides a computer readable medium comprising computer readable instructions that, when executed by a processor, can cause a culture plate scanning system comprising the processor to obtain a first image of a thin film culture device, wherein the first image is produced while illuminating the device with a first ratio of front-side illumination to back-side illumination; obtain a second image of the thin film culture device, wherein the second image is produced while illuminating the device with a second ratio of front-side illumination to back-side illumination that is lower than the first ratio; analyze the first and second images to identify microorganism colonies in each image; analyze the first image to calculate a first value of a size parameter for a colony at a particular location in the culture device; analyze the second image to calculate a second value of the size parameter at the particular location in the culture device; and compare the first value to the second value. In any embodiment, the computer readable medium further can comprise computer readable instructions that, when executed in the processor cause the system to use the first or second image to count a number of microorganism colonies in the culture device. In any embodiment, the computer readable medium further can comprise computer readable instructions that cause the system to use the first and second image to count a number of first type colonies and count a number of second type colonies in the culture device.

Various aspects of the invention may provide a number of advantages. For example, the methods of the present disclosure may improve the accuracy of automated counts of microbial colonies on a culture device. In particular, the rules described herein may address problems that commonly occur, and which can otherwise undermine the accuracy of automated counting of agents on a growth plate.

Additional details of these and other embodiments are set forth in the accompanying drawings and the description below. Other features, objects and advantages will become apparent from the description and drawings, and from the claims.

DETAILED DESCRIPTION

Detection and counting of microorganisms is a universal problem in many diverse fields. Microorganisms occur in almost all foods, in water, in air, and on numerous surfaces and substances with which humans come in contact. Such microorganisms are often harmful and therefore must be measured and controlled.

A widely used practice for detecting the presence of microorganisms in a substance (e.g., food, water, environmental residue) is to place a sample of the substance to be tested, suitably prepared, in a culture device, and to allow the microorganisms to grow into colonies. When cultured in such a medium, colonies become visible to the eye and can be counted. Each visible colony corresponds to one original microorganism. A method of the present disclosure is performed using such culture devices for growing and counting microbial colonies. Typically, the culture device includes an aqueous nutrient medium and a matrix (e.g., a gelling agent such as agar, guar gum, or pectin, for example) to maintain separation of individual colonies. Many culture devices further include indicator compounds as discussed herein. Culture devices for growing and counting microbial colonies include, for example, agar Petri dishes and thin film culture devices sold by 3M Company under the PETRIFILM trade name. PETRIFILM thin film culture devices are disclosed in numerous publications including, for example, U.S. Pat. Nos. 5,364,766; 5,601,998; and 5,681,712; which are all incorporated herein by reference in their entirety.

Many culture media, including typical agar culture media and culture media used in PETRIFILM plates, include indicator compounds to indicate the presence of a microorganism. Indicator compounds include, for example, pH indicators, chromogenic enzyme substrates, and redox indicators. The indicator compounds, when converted directly or indirectly to a product, typically impart a color change to the microbial colony and/or the culture medium surrounding the colony. The color change often makes it easier to detect the presence of the microbial colony in the culture medium (e.g., it improves the color contrast between the colony and the culture medium) and may the color change also may serve to differentiate a particular colony that reacts with a particular indicator compound from another microbial colony that does not react with that indicator compound.

Many types of culture media for growing and differentiating microorganisms include two or more indicator compounds. For example, the culture medium in a PETRIFILM E. coli Count Plate, when hydrated with an aqueous buffer and/or sample, contains a redox indicator (triphenyltetrazolium chloride, hereinafter "TTC") and a chromogenic enzyme substrate (5-bromo-4-chloro-3-indolyl-β-D-glucuronide, hereinafter "X-gluc"). The TTC reacts with microbial cells to form a reddish-colored formazan that stains the cell mass of any bacterial colony that grows in the Gram-negative selective growth medium. In contrast, the X-gluc reacts only with bacteria that, in addition to being able to grow in the selective growth medium, possess β-D-glucuronidase enzyme activity (e.g., E. coli strains that possess β-D-glucuronidase enzyme activity). Hydrolysis of X-gluc causes the formation of an indigo dye, which stains the cell mass of the colony blue and forms a blue halo (i.e. zone of diffusion of the indicator) surrounding the colony having β-D-glucuronidase enzyme activity.

It is contemplated that the method of the present disclosure can be used to distinguish microbial colonies on the basis of their reaction with one or more of a plurality of indicator compounds even if the microbial cells react with the indicator compounds to form products that are substantially the same color. This is possible when the product of one of the indicator compounds remains associated with the cell mass of the microbial colony and the product of another indicator compound diffuses into the culture medium surrounding the cell mass of the colony.

In the method of the present disclosure, the sample is prepared, inoculated into the culture device, and incubated according to procedures that are well known in the art. Sample preparation may optionally include dilution, enzymatic digestion, filtration, and/or sedimentation to reduce or remove nonmicrobial debris from the sample prior to introducing the sample into (e.g., pour-plating) or onto (e.g., surface-plating) the nutrient medium in the culture device.

After a sufficient incubation period at a temperature suitable for the growth of the microorganisms suspected of being present in the sample, microbial colonies can be detected and counted using an imaging system to capture an image of microbial colonies in a culture device and applying various image-analysis schemes. Examples of imaging systems used to count and/or differentiate microbial colonies in a culture device can be found in International Publication No. WO 98/59314; and U.S. Pat. Nos. 7,298,885; 8,094,916; and 7,496,225; which are incorporated herein by reference in their entirety. Examples of image analysis schemes to detect and/or enumerate microbial colonies in a culture device can be found in U.S. Pat. Nos. 6,058,209 and 6,243,486, which are incorporated herein by reference in their entirety.

The present disclosure is directed to techniques for counting microbial colonies in a culture device. The techniques can be used to improve the accuracy of automated counts of microbial colonies in a culture device. The counting rules disclosed herein are typically stored as computer-executable software instructions, and are executed by a processor in a biological scanning system. Alternatively, the rules may be implemented in hardware such as an application specific integrated circuit (ASIC), a field programmable gate array (FPGA), or various hardware components known in the art. The various rules described herein may be applied individually, or in any combination with other counting rules depending on the growth medium being scanned. In any case, by applying the rules described herein, the accuracy of automated counts of microbial colonies on a culture device can be improved.

In any embodiment, a method of the present disclosure employs a system for detecting and counting microbial colonies in a culture device. Systems for detecting and counting microbial colonies in a culture device are described, for example, in International Patent Publication Nos. WO 96/18720, WO 96/18167, WO 2005/062744, which are all incorporated herein by reference in their entirety.

Figure 1:
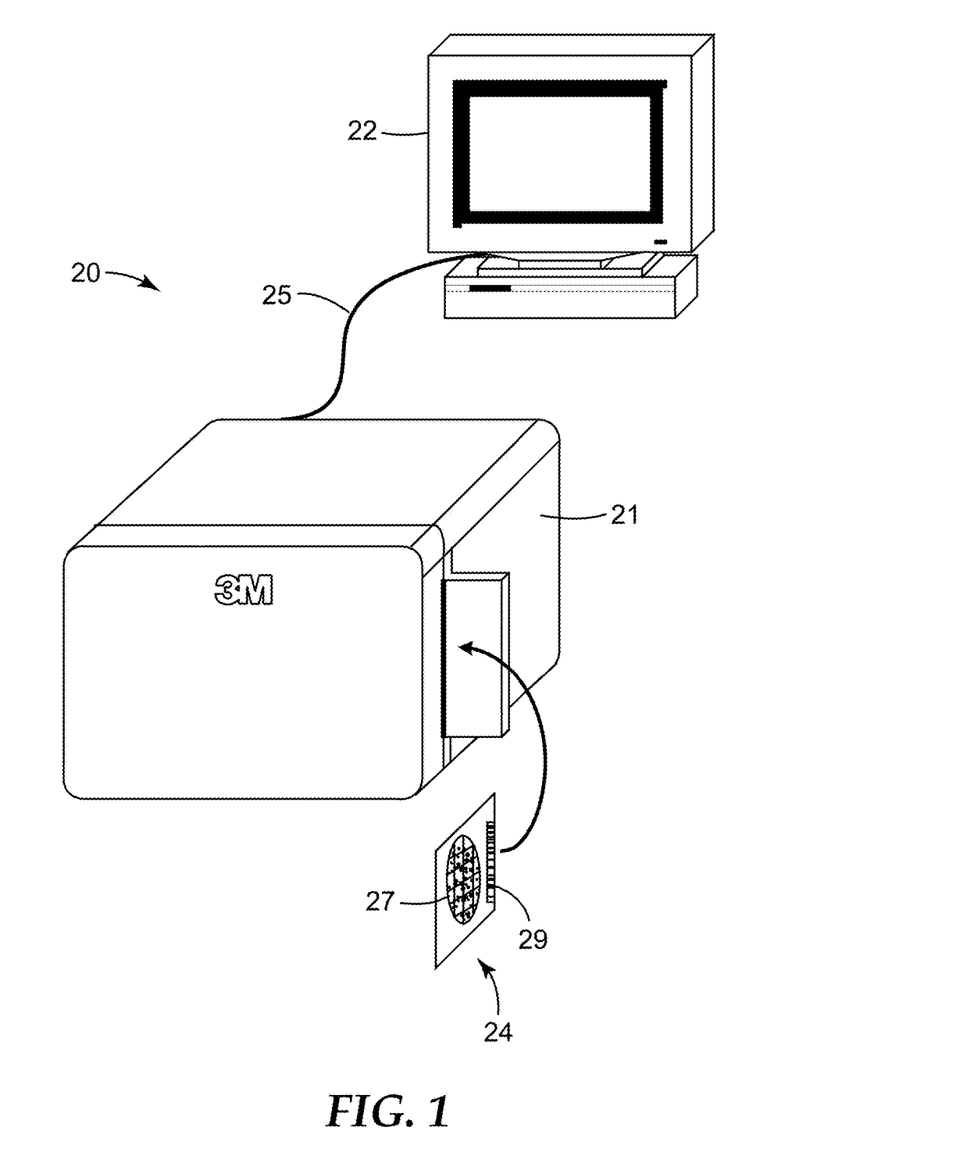
FIG. 1 is a perspective view of an exemplary system comprising a scanning device coupled to an external computer which performs imaging analysis of the images generated by the scanning device.

FIG. 1 shows a perspective view of one embodiment of a system 20 for detecting and counting microbial colonies in a culture device. The system 20 comprises a scanner 21 coupled to an external computer 22 which performs imaging analysis of the images generated by the scanner. External computer 22 may include, for example, a microprocessor programmed for image analysis of a culture device 24. External computer 22 may comprise a personal computer (PC), desktop computer, laptop computer, handheld computer, workstation, tablet personal computing device, mobile device or the like. For example, software programs can be loaded on external computer 22 to facilitate image analysis of images of culture device 24 generated by scanner 21.

Scanner 21 is coupled to external computer 22 via interface 25. Interface 25, for example, may comprise a Universal Serial Bus (USB) interface, a Universal Serial Bus 2 (USB2) interface, an IEEE 1394 Fire Wire interface, a Small Computer System Interface (SCSI) interface, an Advance Technology Attachment (ATA) interface, a serial ATA interface, a Peripheral Component Interconnect (PCI) interface, a conventional serial or parallel interface, wireless connection or the like.

The culture device 24 optionally may include indicia 29, such as a bar code or other type of identification marking used to identify culture device 24. RFID tags, two-dimensional optically detectable codes, or the like, may also be used as indicia. In any case, indicia 29 may identify the type of microorganism being grown and tested on the culture device 24. Scanner 21 can be designed to draw the culture device 24 into scanner 21 to a first location and generate an image of indicia 29, and then draw the culture device 24 to a second location and generate an image of the growth area 27. In this manner, images of indicia 29 and growth area 27 of the culture device can be generated by system 20. Alternatively, a single image may capture both indicia 29 and the growth area 27. In either case, the scanning of indicia 29 can facilitate identification of the type of plate being used so that one or more desirable counting rules can be applied in an automated fashion.

By way of example, the culture device 24 may comprise a thin film culture device sold by 3M under the trade name PETRIFILM plates. Culture device 24 can be utilized to facilitate the rapid growth and detection of microorganisms commonly associated with food contamination, including, for example, aerobic bacteria, *E. coli*, coliform, enterobacteria, yeast, mold, *Staphylococcus aureus, Listeria, Campylobacter*, or the like. Culture devices generally comprise one type of growth medium commonly used for biological growth and bacterial detection and enumeration. The invention, however, may also be applied with a wide variety of other types of growth media.

In any embodiment, the thin film culture device can have a front side that comprises a transparent film cover sheet and a back side comprises a translucent substrate, such as a PETRIFILM *E. coli*/Coliform Count Plate, a PETRIFILM Coliform Count Plate, and a PETRIFILM Enterobacteriaceae Count Plate, for example. Without being bound by theory, it is believed the combination of a relatively thin (e.g., approximately 1-2 mm thick) culture medium disposed between a translucent film and a transparent film provides optical conditions that are beneficial for distinguishing colonies according to the present disclosure.

In order to improve the accuracy of automated counts of microbial colonies on a culture device, various aspects of the method of the present disclosure establishes rules that can be applied during image processing. In other words, the rules described in greater detail below can form part of a colony counting algorithm executed in system 20. The rules may be used individually or in any combination with other image analysis rules (the counting rules described in International Patent Publication No. WO 2005/062744, which is incorporated herein by reference), depending on the type of growth medium being scanned and the problems that may be encountered. Application of one or more of the counting rules can improve a biological scanning system such as system 20 by improving the accuracy of automated counts of microbial colonies on a growth medium such as a thin film culture device or the like.

Figure 2:
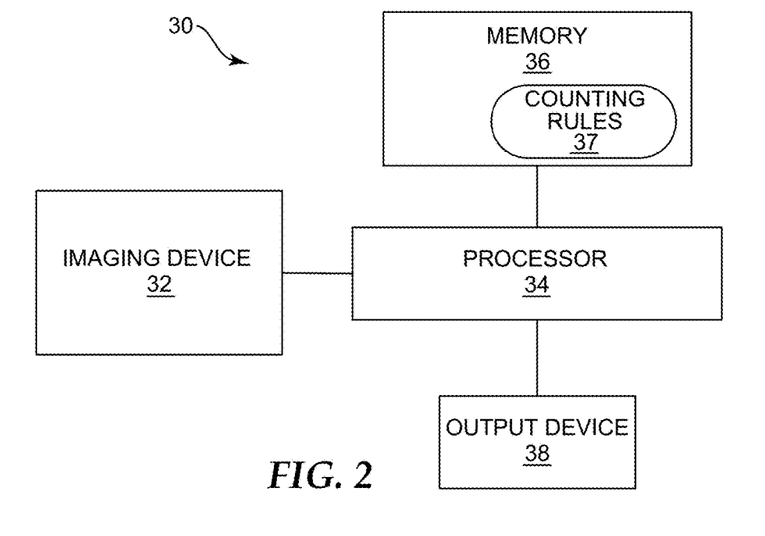
FIG. 2 is a block diagram of a biological scanning system that may correspond to the system illustrated in FIG. 1.

FIG. 2 is a block diagram of a biological scanning system 30, which may correspond to system 20 (FIG. 1). System 30 includes an imaging device 32 that generates one or more images of a growth medium and provides the images to processor 34. Processor 34 is coupled to memory 36. Memory 36 stores various processor-executable software instructions that facilitate image analysis of the images generated by imaging device 32. In particular, memory 36 stores one or more counting rules 37 which are applied during image analysis to improve the accuracy of automated counts of microbial colonies on a culture device. Output device 38 receives the results determined by processor 34 and provides the results to a user.

By way of example, imaging device 32 may comprise a 2-dimensional monochromatic camera for generating one or more images of a culture device. Various illuminators (not shown) may be used to illuminate the front and back of culture device. For example, the illuminators can illuminate the culture device with one or more colors, and one or more images of the culture device can be generated by imaging device 32. In addition, a controller (not shown) can control a ratio of front-side illumination to back side illumination for each image of the culture device. A non-limiting example of an imaging device that provides front-side and back-side illumination that can be used to image a thin film culture device, optionally with a plurality of illumination colors, is described in U.S. Pat. No. 8,094,916, which is incorporated herein by reference in its entirety.

In an embodiment, a first image can be obtained using 100% of the illumination coming from illuminators illuminating the front side of the culture device and 0% of the illumination coming from illuminators illuminating the back side of the culture device and a second image can be obtained using 0% of the illumination coming from illuminators illuminating the front side of the culture device and 100% of the illumination coming from illuminators illuminating the back side of the culture device. In another embodiment, for example, a first image can be obtained using 80% of the illumination coming from illuminators illuminating the front side of the culture device and 20% of the illumination coming from illuminators illuminating the back side of the culture device and a second image can be obtained using 20% of the illumination coming from illuminators illuminating the front side of the culture device and 80% of the illumination coming from illuminators illuminating the back side of the culture device. The ratio of front-side illumination to back-side illumination can be selected to provide optimum contrast for a particular type of nutrient medium in the culture device.

In any embodiment of the method, the first image is produced while illuminating the device with a first ratio (e.g., 100%:0%) of front-side illumination to back-side illumination and the second image is produced while illuminating the device with a second ratio (e.g., 0%:100%) of front-side illumination to back-side illumination that is lower than the first ratio. In any embodiment, the first ratio can be greater than 1:1. In any embodiment, the second ratio can be less than 1:1.

It should be noted that "first image", as used herein, refers to an image that is obtained while the culture device receives illumination primarily from the front side of the plate and "second image", as used herein refers to an image that that is obtained while the culture device receives illumination primarily from the back side of the plate. An implied temporal order of obtaining the images is not intended by the use of the terms "first image" and "second image". Accordingly, a first image of a culture device can be obtained before or after a second image of the culture device. In addition, one of the images (e.g., the first image or second image, respectively) does not need to be obtained by the imaging culture device immediately after obtaining the other image (e.g., the second image or first image, respectively). It is recommended the first and second images are obtained closely enough in time to obviate the possibility of significant biological changes (e.g., growth or enzyme activity) or physical changes (e.g., dehydration) occurring during the intervening time between image acquisitions. Thus, in a preferred embodiment, the first image is obtained within about 30 seconds of the time at which the second image is obtained.

A person having ordinary skill in the art will recognize that, in a system wherein the imaging device is positioned facing the front side of the culture device and the illuminators are also positioned such that the illumination is directed at the front side of the culture device, the image produced by the imaging device substantially comprises light that is reflected from the culture device and the contents thereof. In addition, the person having ordinary skill in the art will also recognize that, in a system wherein the imaging device is positioned facing the front side of the culture device and the illuminators are also positioned such that the illumination is directed at the back side of the culture device, the image produced by the imaging device substantially comprises light that is transmitted by and/or refracted by the culture device and the contents thereof.

The images are provided to processor 34 and may also be stored in memory 36. In any case, the images are analyzed by applying counting rules 37 in order to determine bacteria counts on the culture device. The resolution of imaging device 32 may be approximately 155 pixels per centimeter. In that case, a one centimeter line in the image is 155 pixels long.

Processor 34 may comprise a general-purpose microprocessor that executes software stored in memory 36. Alternatively, processor 34 may comprise an application specific integrated circuit (ASIC) or other specifically designed processor. In any case, processor 34 executes various counting rules 37 to improve the accuracy of automated counts of microbial colonies on a culture device.

Memory 36 is one example, of a computer readable medium that stores processor executable software instructions applied by processor 34. By way of example, memory 36 may comprise random access memory (RAM), read-only memory (ROM), non-volatile random access memory (NVRAM), electrically erasable programmable read-only memory (EEPROM), flash memory, or the like. Counting rules 37 such as those described below, are stored in memory 36 and may form part of a larger software program used for image analysis.

Output device 38 typically comprises a display screen used to communicate results to a user. However, output device 38 could also comprise other types of devices such as a printer or the like. Output device 38 may form part of a scanning unit, such as display (not shown), or may be external to the scanning unit, such as the display screen of external computer 22 (FIG. 1).

Figure 3:
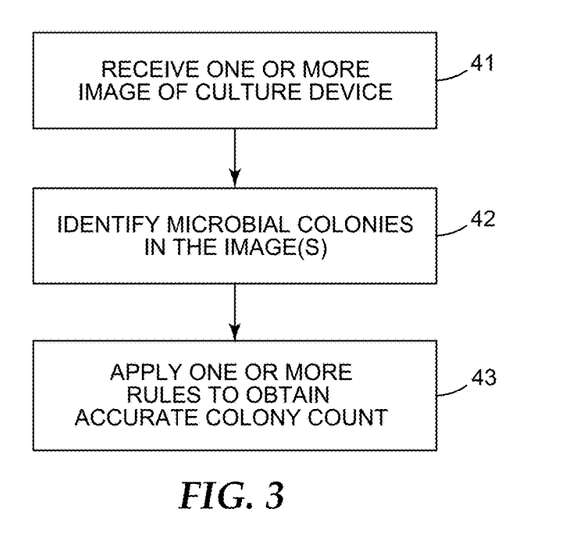
FIG. 3 is a flow diagram illustrating a process of automated analysis of a microbial culture device.

FIG. 3 is a flow diagram illustrating a process of automated culture device analysis. As shown in FIG. 3, processor 34 receives one or more images of a culture device (step 41). Processor 34 invokes various software routines from memory 36 to count the microbial colonies on the culture device (step 42). For example, bacterial colonies may be identified according to a characteristic color they produce after reacting (i.e., directly or indirectly) with one or more indicator compounds in the nutrient medium. Other aspects of colony recognition are discussed below. The software executed by processor 34 can allow for identification of the growth area on the culture device and automated counting of bacterial colonies based on color changes in the growth area where the colonies have grown during incubation.

In accordance with the invention, processor 34 applies one or more rules to improve the accuracy of the count of microbial colonies on the growth medium (step 43). The rules may be applied individually or various combinations of rules may be used, depending on the type of culture device being analyzed. The rules may be individually invoked from memory 36 or may form sub-routines of a larger image analysis software program. The rules may be applied individually or various sets of the rules may be applied. If a set of rules are used, then the order in which the rules are applied may be selected based on the type of plate being scanned. The selected order for application of the rules may affect the end result. Various subsets of the rules may also be applied in any order, and the selected order for a subset of rules may also affect the end result.

Figure 4:
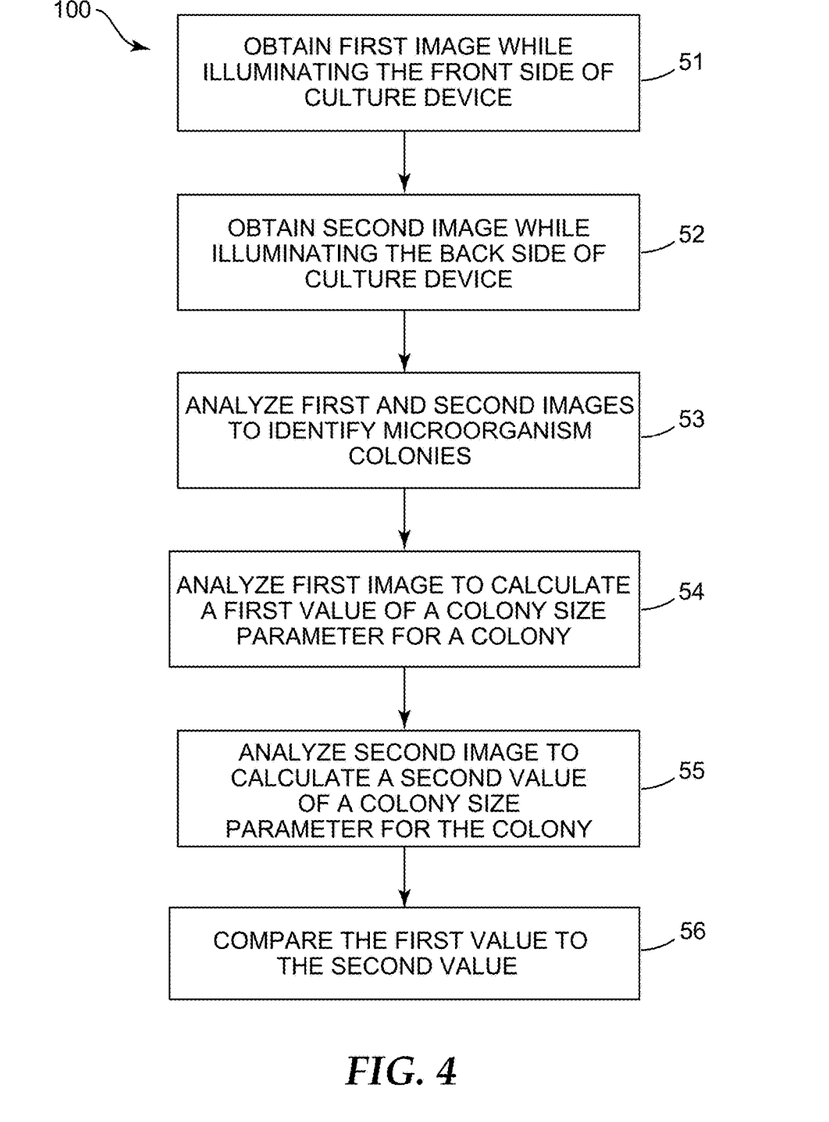
FIG. 4 is a block diagram of one embodiment of a method of analyzing a microbial culture device according to the present disclosure.

FIG. 4 shows one embodiment of a method 100 according to the present disclosure. The method comprises the step 51 of obtaining a first image while illuminating the front side of a culture device and the step 52 of obtaining a second image while illuminating the back side of the culture device. The front side and back side of the culture device can be illuminated with an imaging system as disclosed herein. The method 100 further comprises the step 53 of analyzing the first and second images to identify microorganism colonies in each image.

The first and second images are obtained so as to define objects in the image in shades of at least one color. Thus, analyzing the first and second images to identify microorganism colonies in each image can comprise identifying objects in the image as colonies according to image analysis methods that are well known in the art. For example, Weiss describes techniques to identify microbial colonies in an image based upon one or more criteria including object size, visibility, color, surface quality, and shape (U.S. Pat. No. 6,243,486, which is incorporated herein by reference in its entirety). As discussed above, a method to detect a microbial colony that reacts with an indicator compound comprising TTC can be configured to detect a shade of the color red and a method to detect a microbial colony that reacts with an indicator compound comprising 5-bromo-4-chloro-3-indolyl-β-D-glucuronide can be configured to detect a shade of the color blue.

In a preferred embodiment of the method, a thin film culture device having a second indicator that is a chromogenic enzyme substrate comprising an indolyl group is illuminated from the back-side and an image is taken with an illumination intensity and an integration time (i.e., exposure time) that results in near saturation of the image. Under the conditions of this preferred embodiment, the area in the image defined by the cell mass of a microbial colony can appear to be significantly darker (i.e., permits less transmittance of light) than the zone of colored product (i.e., from the chromogenic enzyme substrate) surrounding the colony. This facilitates the discrimination between the relatively smaller microbial colony from the relatively larger colored zone of colored product (i.e., from the enzyme reaction) surrounding the colony. For example, under these conditions an imaging processor can readily discriminate the edges of the colony mass from the edges of colored product surrounding the colony based on the differences in the color intensity of the regions (e.g., the difference in brightness between the image of the colony and the image of a colored zone surrounding the colony, if present).

Analyzing the first and second images to identify microorganism colonies in each image further comprises identifying the location any colonies detected in the images. The locations will be used to identify and compare measurable parameters associated with coincident colonies in each image. The locations can be identified by X-Y coordinates in each image. Thus, in a preferred embodiment, both the first and second images are obtained without moving or otherwise handling the culture device after the first image is obtained but before the second image is obtained. Alternatively, registration landmarks (e.g., two or more corners of a PETRIFILM plate or registration marks made on any culture device) can be used to orient the images properly in order to determine coincidental colonies in the first and second images.

After analyzing the first image and second image to identify coincidental colonies, the first and second images are analyzed to calculate a value related to a size parameter for each coincidental colony. The size parameter can be, for example, a mean colony diameter, a minimum colony diameter, a maximum colony diameter, or a colony area. Thus a first size parameter value is calculated for a particular colony in the first image (FIG. 4, step 54) and a second size parameter value is calculated for the corresponding coincident colony in the second image (FIG. 4, step 55).

The method 100 further comprises the step (56) of comparing the first size parameter value to the second size parameter value. If the first size parameter value calculated from a first image of a given colony is within a predetermined range (e.g., 80% to 120%, 90% to 110%, or 95% to 105%) of the second size parameter value calculated from a second image of the given colony, the colony is counted as a colony belonging to a first group (e.g., group "A": probable non-*E. coli* microorganisms). In this case, group "A" microorganisms react with a first indicator compound (e.g., TTC) that produces a nondiffusible product but does not react with a second indicator compound (e.g., 5-bromo-4-chloro-3-indolyl-β-D-glucuronide) that produces a diffusible product.

Conversely, if the first size parameter value calculated from a first image of a given colony is greater than the second size parameter value (e.g., at least 20% greater than, at least 50% greater than, or at least 100% greater than the second size parameter value) calculated from the second image of the given colony, the colony is counted as a colony belonging to a second group (e.g., group "B": probable *E. coli* microorganisms). In this case, group "B" microorganisms react with a first indicator compound (e.g., TTC) that produces a nondiffusible product and reacts with a second indicator compound (e.g., 5-bromo-4-chloro-3-indolyl-β-D-glucuronide) to produce a diffusible product, which results in the first size parameter value being greater than the second size parameter value.

Figure 5:
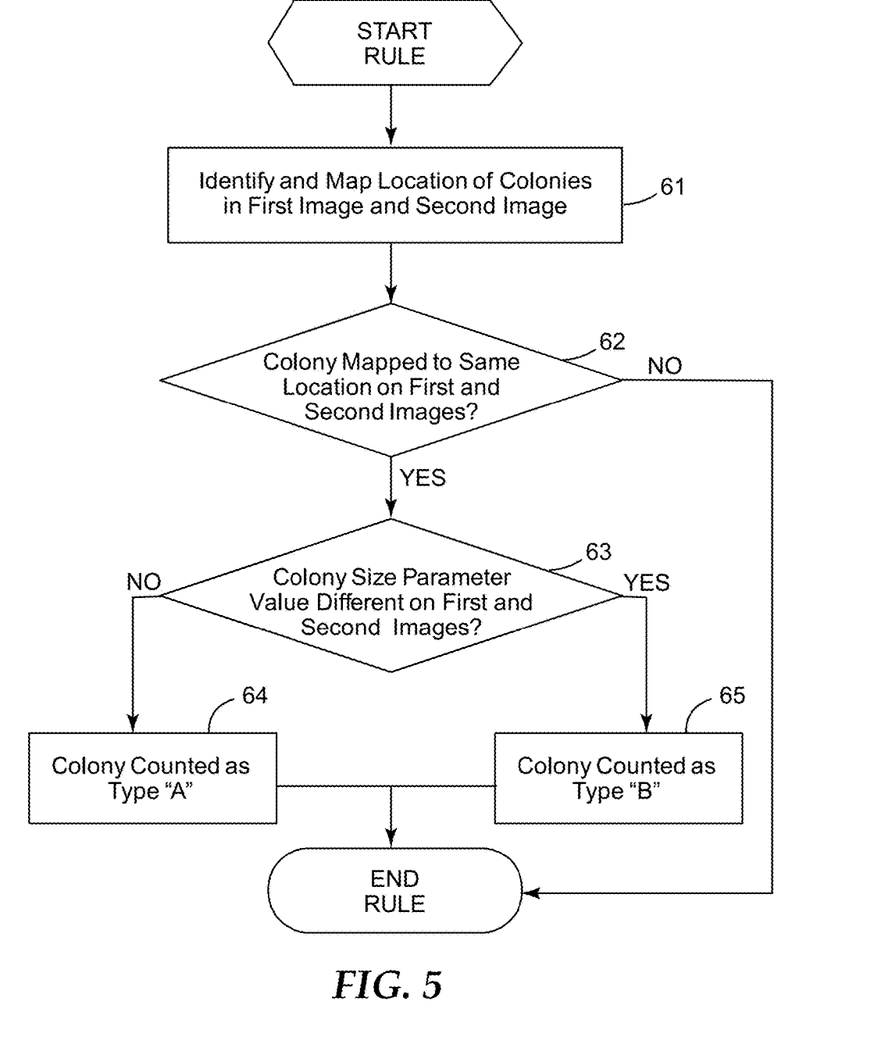
FIG. 5 is a flow diagram of a counting rule to distinguish microbial colony types according to the present disclosure.

FIG. 5 is a flow diagram illustrating the rule for differentiating colonies into a plurality of colony types according to the present disclosure. As illustrated in FIG. 2, processor 34 invokes software stored in memory 36 to identify and map the location of colonies in the first image and second image (step 61). In particular, processor 34 determines whether a colony identified in the first image maps to the same location as a colony identified in the second image (step 62). If coincidental colonies are found in the first and second images, the processor 34 calculates a size parameter value for the coincidental colonies and compares the values to determine whether they are different (step 63). If the values are not different (e.g., within a predetermined range, as discussed above), the colony in the culture device is counted as a first type ("Type A", as indicated in step 64). If the values are different (e.g., the value for the first image is less than the value for the second image), the colony in the culture device is counted as a second type ("Type B", as indicated in step 65). By way of example, a Type "A" colony may react with TTC and not with 5-bromo-4-chloro-3-indolyl-β-D-glucuronide in a PETRIFILM *E. coli*/Coliform Count Plate and, thus, would be identified as a non-*E. coli* colony. Conversely, a Type "B" colony may react with TTC and with 5-bromo-4-chloro-3-indolyl-β-D-glucuronide in a PETRIFILM *E. coli*/Coliform Count Plate and, thus, would be identified as an *E. coli* colony.

Analyzing the images can include RGB (red/green/blue) image processing algorithms. Alternatively, or additionally, analyzing the images can include HSI (hue, saturation, and intensity), HSL (hue, saturation, and lightness), HSV (hue, saturation, and value) algorithms, or combinations thereof.

Figure 6:
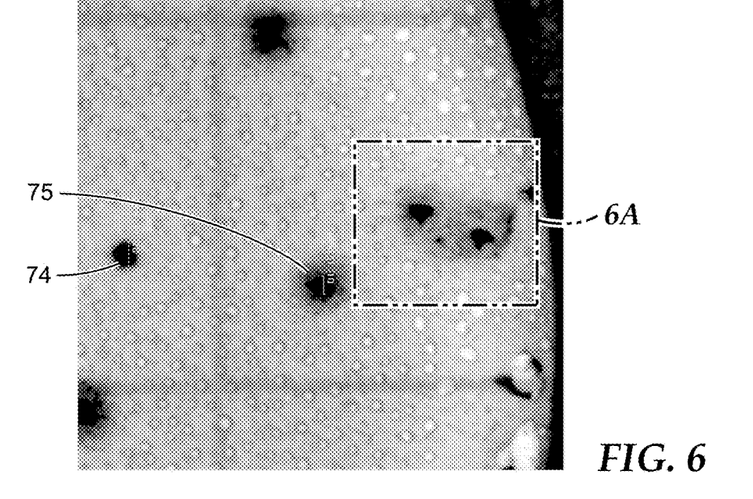
FIG. 6 is a black and white image of a portion of a thin film culture device having two types of microbial colonies growing therein, wherein the image was obtained while illuminating only the back side of the culture device.
Figure 6A:
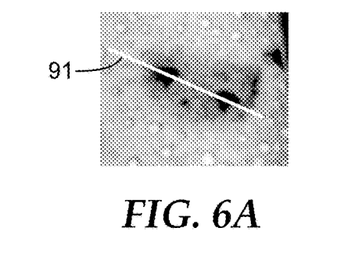
FIG. 6A is a detailed view of a portion of the image of FIG. 6.

FIG. 6 shows a black and white image of a portion of a thin film culture device having two types of microbial colonies growing therein. The image was obtained while illuminating only the back side of the culture device, as described in Example 1. Within the growth area is a plurality of microbial colonies, including colonies of two different types "A" and "B", respectively. Colonies belonging to type "A" react with a first indicator compound that reacts with and stains the cell mass of the bacterial colony. Colonies belonging to type "B" interact with the first compound and, in addition, also react with a second indicator compound that imparts a color change to the microbial colony and/or the culture medium surrounding the colony. The diameters of representative colonies belonging to type A (first colony 74) and type B (second colony 75) were determined according to the technique described in Example 1. The data (listed in Table 1 below) show the diameter of first colony 74 in the back-illuminated image is 22 pixels and the diameter of second colony 75 in the back-illuminated image is 15 pixels. Thus, FIG. 6 shows that, with this type of illumination (i.e., back-side illumination), a size parameter (i.e., the colony diameter) of representative colonies belonging to both types (A and B) may have approximately the same magnitude. Also shown in FIG. 6A is a path 91 of a line scan of a portion of the growth area that includes at least one microbial colony.

Figure 7:
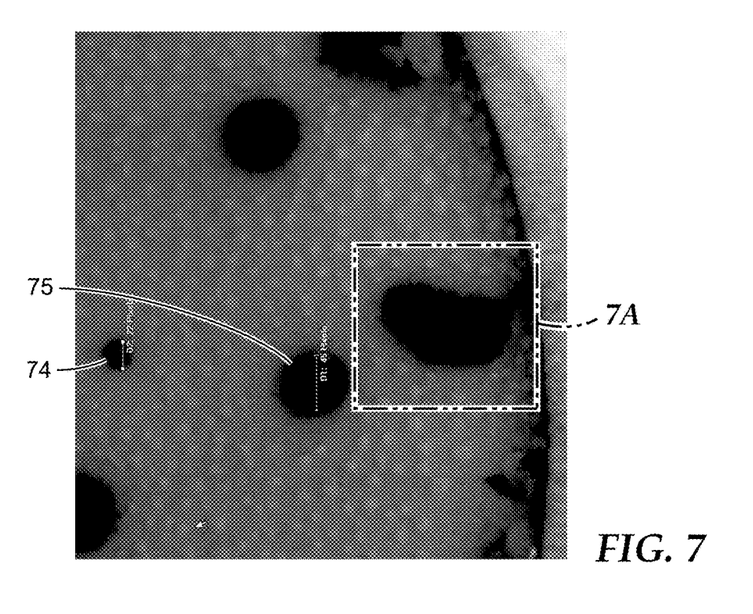
FIG. 7 is a black and white image of the portion of the thin film culture device of FIG. 6, wherein the image was obtained while illuminating only the front side of the culture device.
Figure 7A:
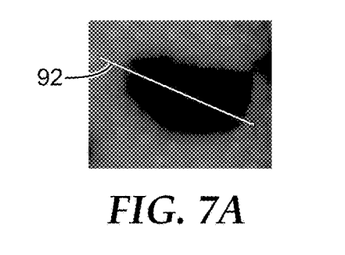
FIG. 7A is a detailed view of a portion of the image of FIG. 7.

FIG. 7 shows a black and white image of the same portion of the thin film culture device shown in FIG. 6. The image was obtained while illuminating only the front side of the culture device, as described in Example 1. The diameters of a first colony 74 and second colony 75 were determined according to the technique described in Example 1. The data show the diameter of first colony 74 in the front-illuminated image is 22 pixels and the diameter of second colony 75 in the front-illuminated image is 45 pixels. Thus, FIG. 7 shows that, with this type of illumination (i.e., front-side illumination), a size parameter (i.e., the colony diameter) of representative colonies belonging to both types (A and B) may have different magnitudes (e.g., substantially different magnitudes). Also shown in FIG. 7A is a path 92 of a line scan of a portion of the growth area that includes at least one microbial colony. Path 92 corresponds to the same pixels as those in path 91 of FIG. 6A.

Figure 8:
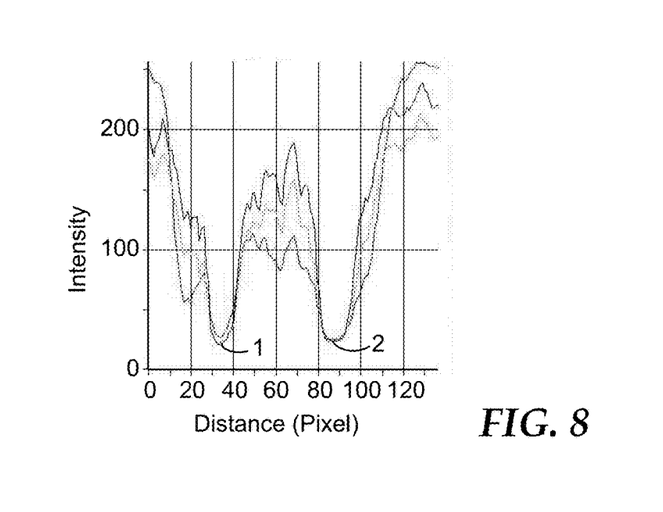
FIG. 8 is a graph of the relative intensities of red, green, and blue components, respectively, of the pixels in the line scan of FIG. 6A.
Figure 9:
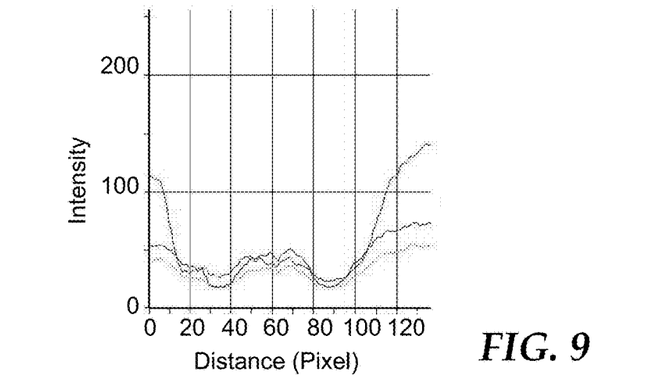
FIG. 9 is a graph of the relative intensities of red, green, and blue components, respectively, of the pixels in the line scan of FIG. 7A.

In order to identify the presence and location of colonies in a back-lit image and to identify the presence and location of microbial colonies in a front-lit image, image-analysis algorithms often analyze the pixels in the digital image line-by-line, comparing the color hue and/or color intensity of a first pixel or first group of pixels to the color hue and/or color intensity of a second pixel proximate the first pixel or second group of pixels proximate the first group of pixels. This type of comparison permits the algorithm to recognize color and/or intensity shifts that may indicate the edge of a microbial colony or other object in the image. FIG. 8 shows a graph of the transmitted pixel intensities for red, green, and blue obtained from pixels along the path 91 in the back-lit image of FIG. 6A. Each of the two negative peaks ("1", and "2", respectively) show that the centers of the respective colonies are darker than the proximate background of the growth medium, thereby clearly indicating the presence of two distinct colonies. FIG. 9 shows a graph of the reflected color intensities for red, green, and blue obtained from pixels along the path 92 in the front-lit image of FIG. 7A. FIG. 9 shows smaller differences in pixel intensities between the pixels comprising the colony centers and the pixels comprising the growth medium adjacent the colonies.

The use of a scanning system with a counting rule for differentiating microbial colonies has been described. The counting rule can be used in a scanning system to improve the accuracy of automated counts of microbial colonies on a culture device.

The techniques have been described as being software-implemented. In that case, a computer readable medium stores processor executable instructions that embody one or more of the rules described above. For example, the computer readable medium may comprise non-transitory computer readable media such as random access memory (RAM), read-only memory (ROM), non-volatile random access memory (NVRAM), electrically erasable programmable read-only memory (EEPROM), flash memory, or the like. The computer readable medium may also comprise a non-volatile memory such as a CD-ROM used to deliver the software to customers. Also, the computer readable medium may comprise an electromagnetic carrier wave, e.g., for delivering the software over a network such as the internet.

The same techniques, however, may also be implemented in hardware. Example hardware implementations include implementations within an application specific integrated circuit (ASIC), a field programmable gate array (FPGA), specifically designed hardware components, or any combination thereof. In addition, one or more of the techniques described herein may be partially executed in hardware, software or firmware.

EMBODIMENTS

Embodiment A is a method, comprising:
using an imaging device to produce a first image of a thin film culture device, the culture device having a front side having a transparent film cover sheet and a back side having a translucent substrate;
  wherein the first image is produced while providing illumination to the front side of the device;
  wherein the culture device comprises first and second indicator compounds;
    wherein the first indicator compound is converted by a microorganism to a first product having a first color;
    wherein the second indicator compound is converted by a microorganism to a water-diffusible second product that forms a second color;

using the imaging device to produce a second image of the thin film culture device, wherein the second image is produced while providing illumination to the back side of the device;

analyzing the first and second images to identify microorganism colonies in each image;

analyzing the first image to calculate a first value of a size parameter for a colony at a particular location in the culture device;

analyzing the second image to calculate a second value of the size parameter at the particular location in the culture device; and comparing the first value to the second value.

Embodiment B is the method of Embodiment A, wherein the first image is produced while illuminating the device with a first ratio of front-side illumination to back-side illumination, wherein the second image is produced while illuminating the device with a second ratio of front-side illumination to back-side illumination that is lower than the first ratio.

Embodiment C is the method of Embodiment B, wherein the first ratio is greater than 1:1.

Embodiment D is the method of Embodiment B, wherein the first ratio is about 100%:0%.

Embodiment E is the method of any one of Embodiments B through D, wherein the second ratio is about 0%:100%.

Embodiment F is the method of any one of the preceding Embodiments, further comprising using the first or second image to count a number of microorganism colonies in the culture device.

Embodiment G is the method of any one of the preceding Embodiments, further comprising using the first and second image to count a number of first type colonies and count a number of second type colonies in the culture device.

Embodiment H is the method of Embodiment G, wherein the first type colonies convert the first indicator to the first product.

Embodiment I is the method of Embodiment G or Embodiment H, wherein the second type colonies convert the second indicator to the second product.

Embodiment J is the method of any one of the preceding Embodiments, wherein the first indicator compound comprises a tetrazolium dye.

Embodiment K is the method of any one of the preceding Embodiments, wherein the second indicator compound comprises a chromogenic enzyme substrate that includes an indolyl group.

Embodiment L is the method of any one of the preceding Embodiments, wherein the size parameter is an observed colony diameter.

Embodiment M is the method of Embodiment L, wherein the colony diameter is a colony minimum diameter.

Embodiment N is a computer readable medium comprising computer readable instructions that, when executed by a processor, cause a culture plate scanning system comprising the processor to:

obtain a first image of a thin film culture device, wherein the first image is produced while illuminating the device with a first ratio of front-side illumination to back-side illumination;

obtain a second image of the thin film culture device, wherein the second image is produced while illuminating the device with a second ratio of front-side illumination to back-side illumination that is lower than the first ratio;

analyze the first and second images to identify microorganism colonies in each image;

analyze the first image to calculate a first value of a size parameter for a colony at a particular location in the culture device;

analyze the second image to calculate a second value of the size parameter at the particular location in the culture device; and compare the first value to the second value.

Embodiment O is the computer readable medium of Embodiment N further comprising computer readable instructions that, when executed in the processor, cause the system to use the first or second image to count a number of microorganism colonies in the culture device.

Embodiment P is the computer readable medium of Embodiment N further comprising computer readable instructions that, when executed in the processor, cause the system to use the first and second image to count a number of first type colonies and count a number of second type colonies in the culture device.

Embodiment Q is a method, comprising:

using an imaging device to produce a first image of a culture device, the culture device having a front side and a back side opposite the front side;
  wherein the first image is produced while providing illumination to the front side of the device;
  wherein the culture device comprises first and second indicator compounds;
    wherein the first indicator compound is converted by a microorganism to a first product having a first color;
    wherein the second indicator compound is converted by a microorganism to a water-diffusible second product that forms a second color;

using the imaging device to produce a second image of the thin film culture device, wherein the second image is produced while providing illumination to the back side of the device;

analyzing the first and second images to identify microorganism colonies in each image;

analyzing the first image to calculate a first value of a size parameter for a colony at a particular location in the culture device;

analyzing the second image to calculate a second value of the size parameter at the particular location in the culture device; and comparing the first value to the second value.

Embodiment R is the method of Embodiment Q, wherein the first image is produced while illuminating the device with a first ratio of front-side illumination to back-side illumination, wherein the second image is produced while illuminating the device with a second ratio of front-side illumination to back-side illumination that is lower than the first ratio.

Embodiment S is the method of Embodiment R, wherein the first ratio is about 100%:0%.

Embodiment T is the method of Embodiment R or Embodiment S, wherein the second ratio is about 0%:100%.

Embodiment U is the method of any one of Embodiments Q through T wherein, while the first and second images are produced, an optical diffuser is disposed proximate the back side of the culture device.

Embodiment V is the method of any one of Embodiments Q through U, further comprising using the first or second image to count a number of microorganism colonies in the culture device.

Embodiment W is the method of any one of Embodiments Q through V, further comprising using the first and second image to count a number of first type colonies and count a number of second type colonies in the culture device.

Embodiment X is the method of Embodiment W, wherein the first type colonies convert the first indicator to the first product.

Embodiment Y is the method of Embodiment W or Embodiment X, wherein the second type colonies convert the second indicator to the second product.

Embodiment Z is the method of any one of claims Q through Y, wherein the first indicator compound comprises a tetrazolium dye.

Embodiment AA is the method of any one of Embodiments Q through Z, wherein the second indicator compound comprises a chromogenic enzyme substrate that includes an indolyl group.

Embodiment BB is the method of any one of Embodiments Q through AA, wherein the first ratio is about 100%:0%, wherein the second ratio is about 0%:100%.

Embodiment CC is the method of any one of Embodiments Q through BB, wherein the size parameter is a colony diameter.

Embodiment DD is the method of Embodiment CC, wherein the colony diameter is a colony minimum diameter.

EXAMPLES

Method for Detecting *E. coli* Colonies

Tryptic Soy Broth (TSB, Catalog # K89) was obtained from Hardy Diagnostics (Santa Maria, Calif.). Microbial strains *E. coli* (ATCC 25922), *E. coli* (3M-FR4), *Salmonella enterica* (ATCC 51812) and *Enterobacter amnigenus* (ATCC 51898) were obtained from Microbiologics Inc (St Cloud, Minn.). An overnight TSB culture was prepared for each microbial strain. Thin film culture devices (3M PETRIFILM *E. Coli*/Coliform Count (EC) Plates) and Butterfield's Phosphate Buffer were both obtained from the 3M Company (St. Paul, Minn.).

Dilutions from overnight cultures of each strain were prepared in Butterfield's Phosphate Buffer to yield approximately 25 colony-forming units (CFU) per mL. The 3M PETRIFILM plates were inoculated by lifting the transparent film cover sheet, pipetting 1 mL of the diluted sample in the center of the coated bottom film, and replacing the cover sheet. The sample was uniformly spread to the desired surface area (approximately 20 cm²) using the spreading device provided by the manufacturer (3M). Inoculated plates were incubated at 35° C. for 24 hours.

The colonies on the PETRIFILM culture plate were imaged and identified using a culture device imaging system. The imaging system contained a centrally positioned glass platen (White Flashed Opal Glass) that served as a platform for placement of the culture plate. The culture plate was illuminated on the front side using two separate sets of light emitting diodes (each set containing two red LEDs, two green LEDs, and two blue LEDs) One set was positioned above to the left (relative to the longitudinal dimension) of the culture plate and the other set was positioned above and to the right (relative to the longitudinal dimension of the culture plate). Light from the LEDs positioned above the culture device was directed away from the culture device and into a light-diffusing reflective surface, which directed a substantially uniform illumination pattern onto the front side of the culture plate. Similarly, the culture plate was illuminated on the back side using two separate sets of light emitting diodes (each set containing two red LEDs, two green LEDs, and two blue LEDs). One set was positioned below and to the left (relative to the longitudinal dimension) of the culture plate and the other set was positioned below and to the right (relative to the longitudinal dimension of the culture plate). Light from the LEDs positioned below the culture device was directed away from the culture device and into a light-diffusing reflective surface, which directed a substantially uniform illumination pattern onto the back side of the glass platen (described above), and created a uniform illumination pattern on the back side of the culture plate.

An Aptina Model MT9P031 CMOS imaging sensor (Aptina Imaging, San Jose, Calif.) was orthogonally-positioned above the platform in order to take images of the culture plate. The imaging sensor and platform were adjusted so that the culture plate was positioned within the focal plane of the sensor. The culture plate was oriented on the platform so that front side (transparent film side) of the culture plate faced the imaging sensor. A black cover was used to isolate the imaging device from room light. The image exposures were selected so that, in the acquired images, less than about 10% of the pixels in a histogram of all of the image pixels were saturated. A first image was taken using only illumination from the front side of the culture plate and a second image was taken using only illumination from the back side of the culture plate. Both images were taken with the culture plate being maintained in exactly the same position on the platform (i.e., the plates were not moved from the platform until both images were acquired). This allowed for the identification of coincidental colonies in the two images by matching the corresponding X-Y coordinate positions.

The two images were analyzed for colony type using ImagePro Plus software (Media Cybernetics, Rockville, Md.). For each image, the size of an individual colony was determined by measuring the colony diameter. The imaging program analyzed for changes in red, green, and blue pixel intensities observed along a line of pixels incorporating the longest dimension of the suspect colony's image. The pixel positions that defined a change in intensity relative to the local background were used to mark the margins of the colony image and to measure the colony diameter (diameter distance was reported as the number of pixels located between the pixel points marking the colony margins). The diameter measurements for coincidental colonies in the two images were then compared to determine the colony type. The results for three representative colonies on the culture plate are presented in Table 1. Colonies designated 1 and 2; respectively correspond to colony 74 and colony 75, respectively in FIGS. 6 and 7.

TABLE 1

| Colony Designation | Colony Diameter (Front-side Illumination) (pixels) | Colony Diameter (Back-side Illumination) (pixels) | Colony Diameter Measured Difference (pixels) | Colony Type** |
|---|---|---|---|---|
| 1 | 22 | 22 | 0 | non-*E. coli* |
| 2 | 45 | 15 | 30 | *E. coli* |
| 3 | 100* | 22 | 78 | *E. coli* |
| 4 | 100* | 23 | 77 | *E. coli* |

*Colony 3 and Colony 4 were both surrounded by a single, diffuse blue halo (i.e., a diffusion zone diffusion of the product of the chromogenic indicator surrounding the colony). Thus, colonies 3 and 4 appeared as a single large colony using front-side illuminated image. However, the back-side illuminated image revealed that there were actually two separate colonies whose blue zones had merged together in the plate
**Colony types were determined based upon the difference between the observed colony diameters measured using front-side-illuminated images compared to the colony diameters measured using back-side-illuminated images.

In any case, various modifications may be made without departing from the spirit and scope of the invention. For example, one or more of the rules described herein may be used with or without other rules and various subsets of the rules may be applied in any order, depending on the desired implementation. These and other embodiments are within the scope of the following claims.

The invention claimed is:

1. A method, comprising:
using an imaging device to produce a first image of a thin film culture device, the culture device having a front side having a transparent film cover sheet and a back side having a translucent substrate;
wherein the first image is produced while providing illumination to the front side of the device;
wherein the culture device comprises first and second indicator compounds;
wherein the first indicator compound is converted by a microorganism to a first product having a first color;
wherein the second indicator compound is converted by a microorganism to a water-diffusible second product that forms a second color;
using the imaging device to produce a second image of the thin film culture device, wherein the second image is produced while providing illumination to the back side of the device;
analyzing the first and second images to identify microorganism colonies in each image;
analyzing the first image to calculate a first value of a size parameter for a colony at a particular location in the culture device;
analyzing the second image to calculate a second value of the size parameter at the particular location in the culture device; and
comparing the first value to the second value.

2. The method of claim 1, wherein the first image is produced while illuminating the device with a first ratio of front-side illumination to back-side illumination, wherein the second image is produced while illuminating the device with a second ratio of front-side illumination to back-side illumination that is lower than the first ratio.

3. The method of claim 2, wherein the first ratio is greater than 1:1.

4. The method of claim 2, wherein the first ratio is about 100%:0%.

5. The method of claim 2, wherein the second ratio is about 0%:100%.

6. The method of claim 1, further comprising using the first or second image to count a number of microorganism colonies in the culture device.

7. The method of claim 1, further comprising using the first and second image to count a number of first type colonies and count a number of second type colonies in the culture device.

8. The method of claim 7, wherein the first type colonies convert the first indicator to the first product.

9. The method of claim 7, wherein the second type colonies convert the second indicator to the second product.

10. The method of claim 1, wherein the first indicator compound comprises a tetrazolium dye.

11. The method of claim 1, wherein the second indicator compound comprises a chromogenic enzyme substrate that includes an indolyl group.

12. The method of claim 1, wherein the size parameter is an observed colony diameter.

13. The method of claim 12, wherein the colony diameter is a colony minimum diameter.

* * * * *